(12) United States Patent
Vigil

(10) Patent No.: US 7,338,463 B2
(45) Date of Patent: Mar. 4, 2008

(54) BALLOON BLADE SHEATH

(75) Inventor: Dennis M. Vigil, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 540 days.

(21) Appl. No.: 10/742,166

(22) Filed: Dec. 19, 2003

(65) Prior Publication Data

US 2005/0137616 A1  Jun. 23, 2005

(51) Int. Cl.
*A61B 17/20* (2006.01)

(52) U.S. Cl. .................................. 604/22; 604/96.01

(58) Field of Classification Search ............... 606/159, 606/170, 192; 604/96.01, 103.07, 103.08, 604/22

See application file for complete search history.

(56) References Cited

U.S. PATENT DOCUMENTS

| | | |
|---|---|---|
| 4,685,458 A | 8/1987 | Leckrone |
| 4,710,181 A | 12/1987 | Fuqua |
| 4,966,604 A | 10/1990 | Reiss |
| 5,042,985 A | 8/1991 | Elliott et al. |
| 5,053,044 A | 10/1991 | Mueller et al. |
| 5,074,841 A | 12/1991 | Ademovic et al. |
| 5,078,725 A | 1/1992 | Enderle et al. |
| 5,092,872 A | 3/1992 | Segalowitz |
| 5,092,873 A | 3/1992 | Simpson et al. |
| 5,116,318 A | 5/1992 | Hillstead |
| 5,156,610 A | 10/1992 | Reger |
| 5,176,693 A | 1/1993 | Pannek, Jr. |
| 5,222,966 A | 6/1993 | Perkins et al. |
| 5,224,949 A | 7/1993 | Gomringer et al. |
| 5,320,634 A | 6/1994 | Vigil et al. |
| 5,372,601 A | 12/1994 | Lary |
| 5,403,334 A | 4/1995 | Evans et al. |
| 5,556,405 A | 9/1996 | Lary |
| 5,616,149 A | 4/1997 | Barath |
| 5,697,944 A | 12/1997 | Lary |
| 5,713,913 A | 2/1998 | Lary et al. |
| 5,728,123 A | 3/1998 | Lemelson et al. |
| 5,792,158 A * | 8/1998 | Lary ........................... 606/159 |
| 5,797,935 A | 8/1998 | Barath |
| 5,941,869 A | 8/1999 | Patterson et al. |
| 6,090,135 A | 7/2000 | Plaia et al. |
| 6,110,192 A | 8/2000 | Ravenscroft et al. |
| 6,258,108 B1 | 7/2001 | Lary |
| 6,306,151 B1 | 10/2001 | Lary |
| 6,309,399 B1 | 10/2001 | Barbut et al. |
| 6,488,693 B2 | 12/2002 | Gannoe et al. |

(Continued)

*Primary Examiner*—LoAn H Thanh
(74) *Attorney, Agent, or Firm*—Vidas, Arrett & Steinkraus, P.A.

(57) ABSTRACT

A sheath is provided to protect a blade when the blade is mounted on a balloon catheter. In particular, this protection is provided while the balloon is deflated for maneuver of the catheter through the vasculature of a patient. The sheath itself is a tubular shaped member that is bifurcated into substantially symmetric halves. Further, the sheath forms a channel for protecting the blade when its halves are juxtaposed. An adhesive bonds both halves of the sheath to the surface of the balloon. When the balloon is deflated, its halves are juxtaposed to cover the blade in the protective channel. On the other hand, when the balloon is inflated, the expanded surface of the balloon pulls the opposed sheath halves that are bonded to it from each other, to thereby expose the blade.

20 Claims, 2 Drawing Sheets

U.S. PATENT DOCUMENTS 6,632,231 B2 10/2003 Radisch, Jr.
2004/0133223 A1* 7/2004 Weber ........................ 606/159
2005/0119678 A1* 6/2005 O'Brien et al. ............. 606/159
2005/0149082 A1* 7/2005 Yee et al. ................... 606/159

* cited by examiner

BALLOON BLADE SHEATH

FIELD OF THE INVENTION

The present invention pertains generally to interventional medical devices. More particularly, the present invention pertains to medical devices that insert cutting blades into the vasculature of a patient. The present invention is particularly, but not exclusively, useful as a sheath for protecting a cutting blade as it is being advanced or withdrawn through the vasculature.

BACKGROUND OF THE INVENTION

Through the years, many medical devices have been developed for the purpose of performing procedures wherein it is necessary to somehow cut or incise the tissue of a patient. For specific applications, interventional devices have been developed that are capable of incising tissue at predetermined locations within the vasculature of a patient. In these cases, it is necessary for the device to be maneuvered through the vasculature. Accordingly, a major consideration involves the prevention of an inadvertent or unwanted cutting or incising of tissue as the device is either being advanced into or withdrawn from the vasculature.

An example of an interventional medical device that has been developed for performing certain in situ procedures of the type mentioned above is disclosed in U.S. Pat. No. 5,556,405. This patent issued to Lary for an invention entitled "Universal Dilator with Reciprocal Incisor", and is assigned to the same assignee as the present invention. As exemplified in this patent, one way to protect against the inadvertent cutting of tissue in the vasculature of a patient is to hold the cutting elements inside a protective housing as it is being moved in the vasculature. Then, while holding the protective housing stationary, an independent mechanism is used to selectively move the cutting elements out of the protective housing so they can be used for cutting. Not all interventional medical devices, however, lend themselves to such a mechanism. For instance, consider a device such as is disclosed in U.S. Pat. No. 5,797,935, which issued to Barath for an invention entitled "Balloon Activated Forced Concentrators for Incising Stenotic Segments" and which is also assigned to the same assignee as the present invention. In such devices, the mechanism that advances the cutting elements (e.g. a balloon) does so by being reconfigured (i.e. inflated). Consequently, an independent protective device that does not accommodate such a reconfiguration and, instead, remains stationary would be inoperative for such a device purpose.

In light of the above, it is an object of the present invention to provide a protective sheath for a blade mounted on an inflatable balloon that is opened by balloon expansion to expose the blade. Another object of the present invention is to provide a protective sheath for a blade mounted on an inflatable balloon that protects the blade from inadvertently cutting tissue as the deflated balloon is maneuvered through the vasculature of a patent. Still another object of the present invention is to provide a protective sheath for a blade mounted on an inflatable balloon that is easy to use, relatively simple to manufacture and comparatively cost effective.

SUMMARY OF THE INVENTION

In accordance with the present invention, a sheath is provided for protecting a blade when the blade is mounted onto the surface of an inflatable balloon. Basically, the sheath of the present invention is an elongated, tubular-shaped member that is affixed to the surface of the balloon. More specifically, this elongated member (sheath) has an outer surface, and it generally defines an axis that lies in a longitudinal plane. Further, the elongated member is bifurcated in this longitudinal plane to create two substantially symmetric halves. Between the halves, the sheath is formed with an axially aligned protective channel for receiving and protecting the blade therein when the halves are juxtaposed to each other.

Structurally, the sheath is bifurcated in the longitudinal plane by the protective channel and a slit that lies in the plane. In detail, the protective channel has opposed channel sides that extend from a common linear vertex in the longitudinal plane to the outer surface of the tube. Also, the slit has opposed sides that extend from the same linear vertex, in a direction away from the protective channel and toward the outer surface of the sheath.

For the operation of the present invention, an adhesive holds the sheath onto the surface of the balloon. Through this connection, the configuration of the sheath depends on the configuration of the balloon. Specifically, when the balloon is deflated, the opposed slit sides of the sheath are juxtaposed against each other to cover the blade inside the protective channel. On the other hand, when the balloon is inflated, and its surface is reconfigured, the opposed sheath halves are separated from each other. This then causes the slit sides to be distanced from each other to expose the blade.

In a preferred embodiment of the present invention the balloon will have substantially three definable portions. These are: a proximal portion; a distal portion; and a central portion that is intermediate the proximal and distal portions. More particularly, the distal and proximal portions are tapered and the intermediate central portion is substantially cylindrical. Specifically, the proximal portion of the balloon is conical shaped with a taper that has a decreasing diameter in the proximal direction. Further, for this preferred embodiment, the blade has a proximal segment that is bonded to the proximal portion of the balloon. The blade also has a distal segment that extends over the central portion of the balloon. This distal segment, however, is not bonded to the balloon. On the other hand, the sheath is bonded to both the proximal and the central portion of the balloon. Consequently, when the balloon is inflated, the sheath will separate as described above. Once exposed by the sheath, the blade becomes inclined relative to the longitudinal axis of the balloon. Specifically, this inclination happens because the proximal segment of the blade is mounted to follow the taper that is established by the proximal portion of the balloon when the balloon is inflated. On the other hand, because it is not bonded to the balloon, the distal segment of the blade will extend outwardly beyond the surface of the balloon.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
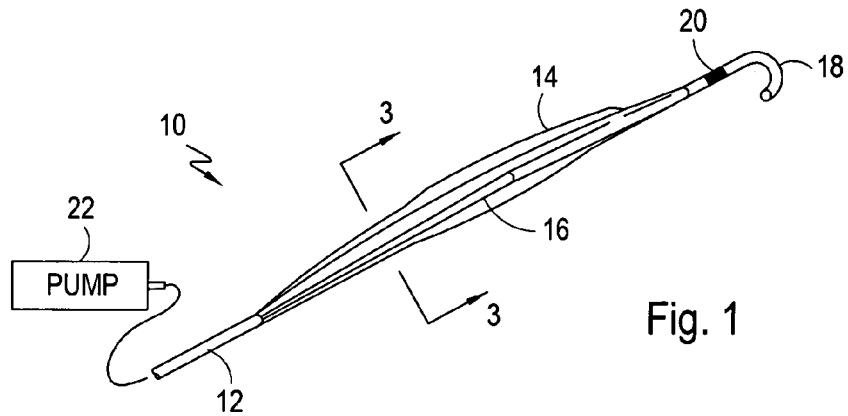
FIG. 1 is a perspective view of a cutting blade balloon catheter system incorporating a protective sheath in accordance with the present invention, with the balloon shown in a deflated configuration.

A system in accordance with the present invention is shown in FIG. 1 and is generally designated 10. As shown, the system 10 includes a catheter 12 and has a balloon 14 that is mounted on the catheter 12. As also shown in FIG. 1, the system 10 includes a sheath (elongated member) 16 that is bonded to the balloon 14 in a manner well known in the pertinent art, such as by solvent bonding. For purposes of the present invention, the sheath 16 is made of a polymer material of a type well known in the art. Further, the catheter 12 is formed with a so-called "pig tail" tip 18 that can be used to facilitate the maneuvering of the catheter 12 within the vasculature of a patient (not shown). Also, catheter 12 is shown to include a radiopaque marker 20 for locating the catheter 12 once it is in the vasculature. FIG. 1 also indicates that an extracorporeal fluid pump 22 is connected in fluid communication with the balloon 14 to selectively inflate and deflate the balloon 14. In detail, the structure of sheath 16 will be best appreciated by referencing FIG. 2.

Figure 2:
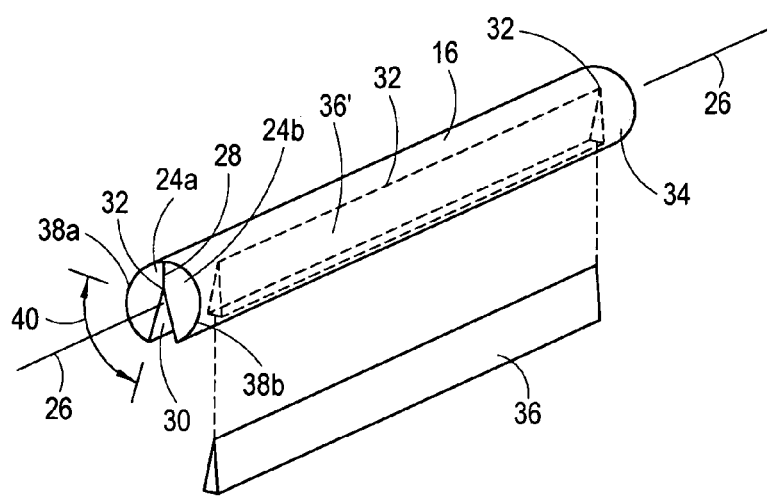
FIG. 2 is an exploded perspective view of the interaction between the protective sheath and a cutting blade.

In FIG. 2 it will be seen that the sheath (elongated member) 16 is effectively bifurcated into two halves 24a and 24b. Further, the sheath 16 is generally a tube shaped structure that defines a longitudinal axis 26. Importantly, the sheath 16 is divided by a slit 28 and is formed with a protective channel 30. As shown, both the slit 28 and the protective channel 30 extend lengthwise along the sheath 16 in a longitudinal direction. In more detail, the slit 28 extends radially from the axis 26 and lies in a longitudinal plane that is generally defined by the axis 26 and the slit 28. Structurally, the slit 28 extends from a vertex 32 to the outer surface 34 of the sheath 16 wherein the vertex 32 is substantially parallel to the axis 26 and is in the longitudinal plane.

As shown in FIG. 2, the protective channel 30 of sheath 16 is diametrically opposed to the slit 28. Like the slit 28, the protective channel 30 extends from the vertex 32 to the outer surface 34. Importantly, the dimensions of the protective channel 30 are established to conform the channel 30 to the dimensions of a blade 36. Stated differently, the protective channel 30 is formed to receive the blade 36 therein, such as is shown for the phantom blade 36' in FIG. 2. As envisioned for the present invention, the blade 36 will be preferably made of a stainless steel and will be approximately twenty-five millimeters in length.

Still referring to FIG. 2, it will be appreciated that the sheath 16 has a bonding area 38a on the half 24a, and a similar bonding area 38b on the half 24b. Both of these bonding areas 38a and 38b are located on the outer surface 34 of the sheath 16 and extend along the length of the sheath 16. Further, these bonding areas 38a and 38b extend on the surface 34 through an arc length 40 that is approximately ninety degrees, or more. An adhesive that is placed on the bonding areas 38a and 38b bonds the sheath 16 to the balloon 14. More specifically, this is done with the blade 36 also bonded to the balloon 14 and with the blade 36 positioned inside the protective channel 30. Importantly, throughout the operation of the present invention, the outer surface 34 of the sheath 16 remains bonded to the balloon 14 at the bonding areas 38a and 38b. Likewise, the blade 36 also remains operationally bonded to the balloon 14.

Figure 3A:
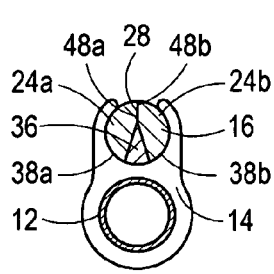
FIG. 3A is a cross-sectional view of the system for a single blade and its protective sheath as seen along the line 3-3 in FIG. 1.
Figure 3B:
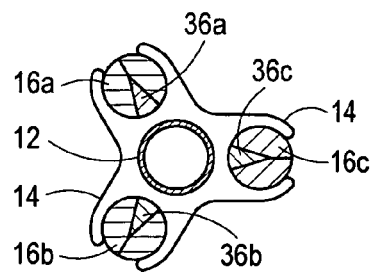
FIG. 3B is a cross-sectional view of the system for a plurality of blades and their respective protective sheaths as would be seen along the line 3-3 in FIG. 1.

By cross-referencing FIG. 1 with FIG. 3A it will be noted that when the balloon 14 is deflated, the sheath 16 effectively holds and covers the blade 36 in its protective channel 30. Further, in this configuration, the sheath 16 also helps define folds for the deflated balloon 14 that reduce the profile of balloon 14, and thereby facilitate the maneuvering of the catheter 12 through the vasculature. As indicated by FIG. 3B, although the disclosure here is directed toward a single sheath 16 and blade 36 combination, the present invention also contemplates the use of a plurality of such combinations. The combinations of multi-blades 36a,b,c and respective multi sheaths 16a,b,c shown in FIG. 3B are only exemplary.

Figure 4:
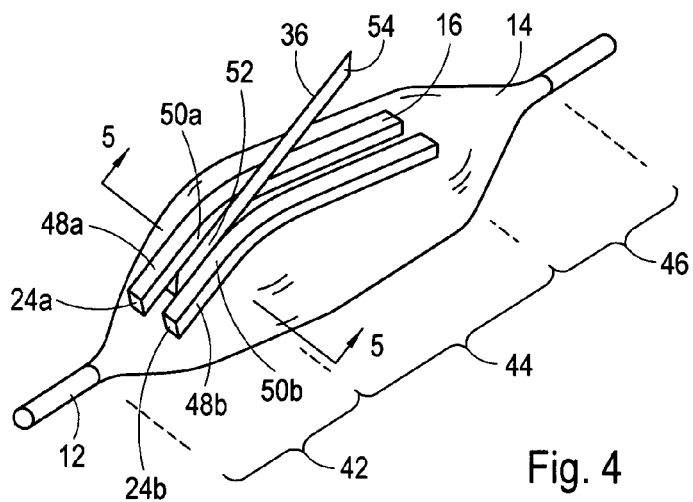
FIG. 4 is a perspective view of the cutting blade balloon catheter system shown in FIG. 1, with the balloon in an inflated configuration.

As shown in FIG. 4, after the balloon 14 has been inflated by pump 22, it has three definable portions. These are: a proximal portion 42; and intermediate portion 44; and a distal portion 46. In detail, the intermediate portion 44 is substantially cylindrical shaped. On the other hand, both the proximal portion 42 and the distal portion 46 are conical shaped. Specifically, the proximal portion 42 is characterized by a taper having a decreasing diameter in the proximal direction.

In the operation of the system 10 of the present invention, the catheter 12 and balloon 14 are advanced into the vasculature of a patient. Accordingly, the sheath 16 and blade 36 that are respectively attached to the balloon 14 as disclosed above are also advanced into the vasculature. This is done while the balloon 14 is in its deflated configuration (see FIG. 1). Once the system 10 has been advanced into the vasculature, the balloon 14 can be selectively inflated into its inflated configuration (see FIG. 4).

Figure 5:
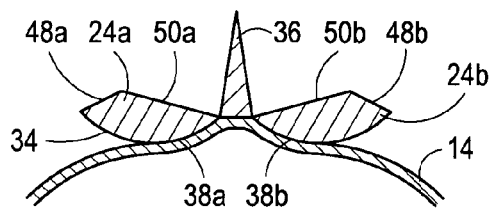
FIG. 5 is a partial cross-sectional view of the system as seen along the line 5-5 in FIG. 4.

The consequence of inflating balloon 14 is perhaps best appreciated by cross-referencing FIG. 3A (deflated configuration) with FIG. 4 (inflated configuration). This appreciation may be further enhanced by also referencing FIG. 5. In overview, as the balloon 14 is inflated, the halves 24a and 24b of the sheath 16 are separated from each other. Recall, the halves 24a and 24b are individually bonded to the surface of the balloon 14. Accordingly, because this fixed relationship between balloon 14 and the halves 24a and 24b has been previously established, and is maintained, the reconfiguration of balloon 14 (i.e. the inflation of balloon 14) causes the respective halves 24a and 24b to separate. In detail, when the balloon 14 is deflated (FIG. 3A), the sides 48a and 48b of slit 28 are juxtaposed with each other to confine and cover the blade 36 in the protective channel 30 of sheath 16. On the other hand, when balloon 14 is inflated (FIGS. 4 and 5), the slit sides 48a and 48b are separated from each other. Similarly, the sides 50a and 50b of protective channel 30 are distanced from the blade 36. The result of all this is that the blade 36 is exposed for operational use as desired.

After the operational use of an exposed blade 36 has been completed, the balloon 14 may be deflated by appropriately manipulating the pump 22. This causes the balloon 14 to return from its inflated configuration (FIG. 4) to its deflated configuration (FIGS. 1 and 3A). As implied above, during this deflation, the interaction between the sheath 16 and the balloon 14 will cause the balloon 14 to advantageously fold along predetermined fold lines. Also, the blade 36 will again be enclosed within the protective channel 30 as the system 10 is safely withdrawn from the vasculature of a patient.

Figure 6:
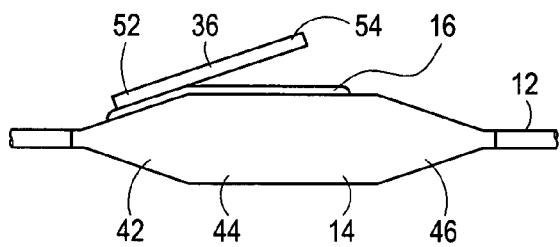
FIG. 6 is a side elevation view of a preferred embodiment of the present invention.
Figure 7:
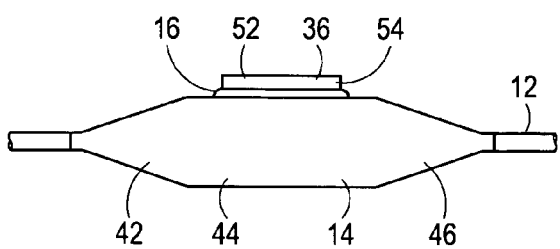
FIG. 7 is a side elevation view of an alternate embodiment of the present invention.

As contemplated by the present invention, a preferred embodiment for the system 10 provides for a tilting blade 36 (see FIGS. 4 and 6). As perhaps best seen in FIG. 6, for this embodiment of the system 10, although a proximal segment 52 of the blade 36 is bonded to the proximal portion 42 of the balloon 14, a distal segment 54 of the blade 36 is not. Consequently, because the distal segment 54 of blade 36 is not bonded to the balloon 14, the blade 36 will follow the taper of proximal portion 42. Thus, the distal segment 54 of blade 36 will extend radially from the balloon 14. The distal segment 54 will, however, be enclosed in the protective channel 30 and covered by sheath 16, as disclosed above, whenever balloon 14 is deflated. In an alternate embodiment of the system 10 of the present invention, as seen in FIG. 7, the blade 36 and sheath 16 may be mounted directly onto the intermediate portion 44 of balloon 14. In this case, the entire blade 36 will move through a same radial distance as the balloon 14 is inflated.

While the particular Balloon Blade Sheath as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A sheath for protecting a blade which comprises:
   an elongated member having an outer surface and defining an axis lying in a longitudinal plane, the elongated member being formed with an axially aligned protective channel for receiving the blade therein, with the channel being bounded by opposed channel sides extending from a common vertex to the outer surface of the elongated member, wherein the vertex is substantially parallel to the axis, and wherein the elongated member is formed with a slit in the longitudinal plane with the slit having opposed slit sides extending from the vertex and away from the protective channel to the outer surface of the elongated member;
   an expansion means having a surface moveable between a first configuration and a second configuration; and
   a means for holding the elongated member on the surface of the expansion means with the slit sides juxtaposed to each other for covering the blade in the protective channel when the surface of the expansion means is in its first configuration, and with the slit sides separated from each other to expose the blade when the surface of the expansion means is in its second configuration.

2. A sheath as recited in claim 1 wherein the elongated member is made of a polymer material.

3. A sheath as recited in claim 1 wherein the elongated member is substantially cylindrical shaped.

4. A sheath as recited in claim 3 wherein the holding means is an adhesive placed on a bonding area of the elongated member, and wherein the bonding area extends azimuthally on the outer surface of the elongated member from the protective channel.

5. A sheath as recited in claim 4 wherein the bonding area extends through an arc distance of approximately ninety degrees.

6. A sheath as recited in claim 1 wherein the blade is bonded to the surface of the expansion means.

7. A sheath as recited in claim 1 wherein the expansion means is a balloon.

8. A sheath as recited in claim 7 wherein a proximal portion of the balloon is conical shaped with a taper having a decreasing diameter in a proximal direction, and wherein the blade has a proximal segment and a distal segment, with the proximal segment of the blade bonded to the surface of the balloon in the proximal portion of the balloon.

9. A system which comprises:
   an elongated balloon defining an axis and having a surface moveable between a first configuration and a second configuration;
   a means for moving the balloon between a deflated configuration and an inflated configuration;
   at least one blade axially aligned and mounted on the surface of the balloon for movement therewith;
   an elongated member having an outer surface and defining an axis lying in a longitudinal plane, the elongated member being formed with an axially aligned protective channel for receiving the blade therein, with the channel being bounded by opposed channel sides with each channel side extending from a common vertex in the longitudinal plane to the outer surface of the elongated member, wherein the vertex is substantially parallel to the axis of the elongated member, and wherein the elongated member is formed with a slit the slit being substantially diametrically opposed to the protective channel and bounded by opposed slit sides with each slit side extending in the longitudinal plane from the vertex to the outer surface of the elongated member; and
   an adhesive for holding the elongated member on the surface of the balloon with the slit sides juxtaposed to each other for covering the blade in the protective channel when the surface of the balloon is in its deflated configuration, and with the slit sides separated from each other to expose the blade when the surface of the balloon is in its inflated configuration.

10. A system as recited in claim 9 wherein there is a plurality of blades mounted on the surface of the balloon with a respective elongated member for each blade.

11. A system as recited in claim 9 wherein the elongated member is made of a polymer material and is substantially cylindrical shaped, and further wherein the adhesive is placed on a bonding area of the elongated member, with the bonding area extending azimuthally on the outer surface of the elongated member away from the protective channel.

12. A system as recited in claim 9 wherein a proximal portion of the balloon is conical shaped with a taper having a decreasing diameter in a proximal direction, and wherein the blade has a proximal segment and a distal segment, with the proximal segment of the blade bonded to the surface of the balloon in the proximal portion of the balloon.

13. A system as recited in claim 12 wherein the balloon has a proximal end and a distal end and the elongated member extends therebetween.

14. A system as recited in claim 9 further comprising a radiopaque marker mounted on said system for determining a location for the balloon.

15. A system as recited in claim 9 wherein the blade is made of stainless steel and is approximately twenty five millimeters in length.

16. A method for using a sheath to protect a blade mounted on an inflatable balloon during maneuver of the balloon through the vasculature of a patient which comprises the steps of:

providing a sheath having an outer surface and defining an axis lying in a longitudinal plane, the sheath being formed with an axially aligned protective channel for receiving the blade therein, with the channel being bounded by opposed channel sides extending from a common vertex to the outer surface of the sheath, wherein the vertex is substantially parallel to the axis, and wherein the sheath is formed with a slit in the longitudinal plane with the slit having opposed slit sides extending from the vertex and away from the protective channel to the outer surface of the sheath;

mounting the sheath on the surface of the balloon wherein the balloon surface is moveable between a deflated configuration and an inflated configuration;

holding the sheath on the surface of the balloon with the slit sides juxtaposed to each other for covering the blade in the protective channel when the surface of the balloon is in its deflated configuration; and selectively inflating the balloon to separate the slit sides from each other to expose the blade with the surface of the balloon in its inflated configuration.

17. A method as recited in claim 16 further comprising the step of applying an adhesive to a bonding area of the sheath to hold the sheath on the surface of the balloon, wherein the bonding area extends azimuthally from the protective channel through an arc distance of approximately ninety degrees on the outer surface of the sheath.

18. A method as recited in claim 17 wherein a proximal portion of the balloon is conical shaped with a taper having a decreasing diameter in a proximal direction, and wherein the blade has a proximal segment and a distal segment, with the proximal segment of the blade bonded to the surface of the balloon in the proximal position of the balloon.

19. A method as recited in claim 17 wherein an intermediate portion of the balloon is cylindrical shaped, and wherein the blade is bonded to the surface of the balloon in the proximal portion of the balloon.

20. A method as recited in claim 16 wherein the balloon is made of a polymer.

* * * * *